(12) United States Patent
Bouvier et al.

(10) Patent No.: US 9,050,581 B2
(45) Date of Patent: Jun. 9, 2015

(54) AGGREGATE ZEOLITIC ABSORBENTS, THEIR METHOD OF PREPARATION AND THEIR USES

(75) Inventors: Ludivine Bouvier, Billere (FR); Stéphane Kieger, Sartrouville (FR); Catherine Laroche, Vernaison (FR); Philibert Leflaive, Mions (FR); Tom Frising, Lyons (FR)

(73) Assignees: CECA S.A., La Garenne Colombes (FR); Institut Francais Du Petrole, Rueil Malmaison (FR)

( * ) Notice: Subject to any disclaimer, the term of this patent is extended or adjusted under 35 U.S.C. 154(b) by 898 days.

(21) Appl. No.: 12/808,073

(22) PCT Filed: Dec. 16, 2008

(86) PCT No.: PCT/FR2008/052317
§ 371 (c)(1),
(2), (4) Date: Sep. 15, 2010

(87) PCT Pub. No.: WO2009/081024
PCT Pub. Date: Jul. 2, 2009

(65) Prior Publication Data
US 2011/0124942 A1 May 26, 2011

(30) Foreign Application Priority Data

Dec. 20, 2007 (FR) ...................... 07 60098

(51) Int. Cl.
| | |
|---|---|
| *B01J 20/18* | (2006.01) |
| *B01J 29/80* | (2006.01) |
| *C07C 7/13* | (2006.01) |
| *C07C 17/389* | (2006.01) |
| *B01J 20/28* | (2006.01) |
| *C07C 29/76* | (2006.01) |
| *C07C 37/82* | (2006.01) |
| *C07C 201/16* | (2006.01) |

(52) U.S. Cl.
CPC .............. *B01J 20/18* (2013.01); *B01J 20/183* (2013.01); *B01J 20/186* (2013.01); *B01J 20/28004* (2013.01); *B01J 20/2803* (2013.01); *C07C 7/13* (2013.01); *C07C 17/389* (2013.01); *C07C 29/76* (2013.01); *C07C 37/82* (2013.01); *C07C 201/16* (2013.01)

(58) Field of Classification Search
USPC ................... 502/64, 67, 69, 73, 79, 407, 414; 423/700, 713; 585/820, 826, 828, 831; 536/127; 568/700, 758
See application file for complete search history.

(56) References Cited

U.S. PATENT DOCUMENTS

| | | | |
|---|---|---|---|
| 2,882,244 A | 4/1959 | Milton | |
| 2,985,589 A | 5/1961 | Broughton et al. | |
| 3,130,007 A | 4/1964 | Breck | |
| 3,558,730 A | 1/1971 | Neuzil | |
| 3,558,732 A | 1/1971 | Neuzil | |
| 3,626,020 A | 12/1971 | Neuzil | |
| 3,663,638 A | 5/1972 | Neuzil | |
| 6,410,815 B1 * | 6/2002 | Plee et al. ...................... 585/828 |
| 6,884,918 B1 * | 4/2005 | Plee et al. ...................... 585/828 |
| 8,530,367 B2 | 9/2013 | Bouvier et al. | |
| 2005/0170947 A1 * | 8/2005 | Plee et al. ........................ 502/64 |
| 2008/0156190 A1 * | 7/2008 | Lutz et al. ....................... 95/148 |

FOREIGN PATENT DOCUMENTS

| | | |
|---|---|---|
| FR | 2903978 A1 | 1/2008 |
| WO | WO 99/10096 A1 | 3/1999 |
| WO | WO 00/50166 A1 | 8/2000 |
| WO | WO 01/24923 A1 | 4/2001 |
| WO | WO 2008/009845 A1 | 1/2008 |

OTHER PUBLICATIONS

International Search Report corresponding to International Application No. PCT/FR2008/052317 dated Jun. 26, 2009.
Written Opinion corresponding to International Application No. PCT/FR2008/052317 dated Jun. 26, 2009.

* cited by examiner

*Primary Examiner* — Elizabeth Wood
(74) *Attorney, Agent, or Firm* — McDonnell Boehnen Hulbert & Berghoff LLP

(57) ABSTRACT

The present invention relates to aggregate zeolitic adsorbents based on zeolite X and zeolite LSX.

These adsorbents are particularly suitable for separating $C_8$ aromatic isomers and in particular xylenes, separating sugars, separating polyhydric alcohols, separating isomers of substituted toluenes, separating cresols, separating dichlorobenzenes.

31 Claims, 1 Drawing Sheet

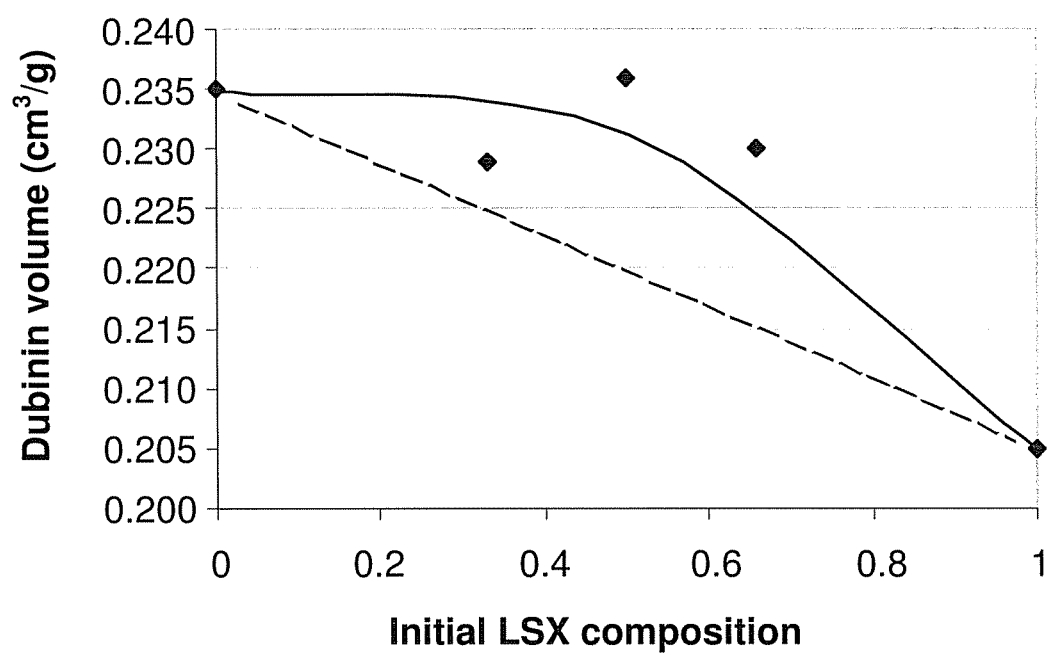

AGGREGATE ZEOLITIC ABSORBENTS, THEIR METHOD OF PREPARATION AND THEIR USES

RELATED APPLICATIONS

The application is the U.S. National Stage of PCT/FR2008/052317, filed Dec. 16, 2008, which claims priority to French application No. 0760098, filed Dec. 20, 2007.

The invention relates to aggregate zeolitic adsorbents based on a mixture of zeolite X powder and zeolite LSX powder, exchanged with barium or exchanged with barium and with potassium.

These adsorbents may be used more particularly for producing highly pure paraxylene, from an aromatic hydrocarbon feedstock containing isomers with 8 carbon atoms.

The use of zeolitic adsorbents consisting of X or Y zeolites exchanged with ions such as barium, potassium or strontium, alone or in a mixture, for selectively adsorbing paraxylene from a mixture of aromatic hydrocarbons, is well known from the prior art.

U.S. Pat. No. 3,558,730, U.S. Pat. No. 3,558,732, U.S. Pat. No. 3,626,020 and U.S. Pat. No. 3,663,638 show that adsorbents comprising aluminosilicates exchanged with barium or potassium or with barium alone (U.S. Pat. No. 3,960,774) are effective for separating paraxylene from a $C_8$ aromatic cut.

A method for preparing these adsorbents is described for example in U.S. Pat. No. 3,878,127 and consists in treating, in hot caustic soda, aggregates (zeolite X+binder) having a $Na_2O/Al_2O_3$ ratio that is strictly lower than 0.7 in order to replace the exchangeable cations of the zeolite (such as the protons or cations of group IIA), by sodium prior to an exchange with barium and/or barium+potassium, the prior exchange with sodium enabling a larger quantity of barium or barium plus potassium ions to be added to the zeolitic structure.

These adsorbents are used as adsorption agents in liquid phase processes, preferably of the simulated countercurrent type, similar to those described in U.S. Pat. No. 2,985,589, which apply to aromatic $C_8$ cuts, among others.

The zeolites encountered in the prior art for separating xylenes belong to the structural type of faujasite, first described in U.S. Pat. No. 2,882,244 and U.S. Pat. No. 3,130,007, which are crystallized silicoaluminates having cages with perfectly defined size, connected in the three dimensions.

U.S. Pat. No. 6,884,918 recommends a faujasite X with a Si/Al atomic ratio of between 1.15 and 1.5. U.S. Pat. No. 6,410,815 teaches that zeolitic adsorbents based on faujasite having a low silica content, that is, having a Si/Al atomic ratio close to 1 (which we shall call LSX, an abbreviation of Low Silica X), are advantageously used for separating paraxylene.

Zeolite X and Zeolite X having a low silica content therefore both have good performance in terms of selectivity for paraxylene, but the synthesis of low silica content zeolite X is rather difficult in comparison with the synthesis of zeolite X. In fact, to lower the Si/Al atomic ratio of a zeolite of the faujasite type, the consumption of caustic soda used in the zeolite synthesis method must be increased. Moreover, to crystallize in accordance with the faujasite structural type, when the Si/Al atomic ratio is 1, high concentrations of caustic potash must be added to inhibit the formation of zeolite A and to obtain low silica zeolite X exclusively. These high caustic soda and caustic potash consumptions increase the production cost of this type of zeolite and raise problems of effluent releases.

In the references listed above, the zeolitic adsorbents are in the form of powder or in the form of aggregates mainly consisting of zeolite and up to 15 to 20% by weight of inert agglomeration binder.

Since zeolites X and X with low silica content are usually synthesized by nucleation and crystallization of silicoaluminate gels, the powders produced are particularly difficult to use on the industrial scale (high pressure drops during handling operations), and the aggregate forms are preferred, for example in the form of granules or grains, which do not have the drawbacks inherent in powdery materials.

These aggregates, whether in platy, bead or extruded form, generally consist of a zeolite, which constitutes the active element (in the context of adsorption) and a binder for obtaining the cohesion of the zeolite crystals on the aggregates and for conferring thereon sufficient mechanical strength to withstand the vibrations and movements to which they are subjected during their processing.

These aggregates are prepared for example by pasting zeolite powder with a clay paste, in proportions of about 80 to 90% by weight of zeolite powder for 20 to 10% by weight of binder, followed by shaping into bead, platy or extruded form, and heat treatment at high temperature for baking the clay and reactivating the zeolite, the barium exchange being carried out before and/or after the agglomeration of the zeolite powder with the binder.

Zeolitic aggregates are obtained having a particle size distribution of a few millimeters in general, and which, if the choice of the binder and the granulation are carried out according to the rules of the art, have a set of satisfactory properties, in particular porosity, mechanical strength, and abrasion resistance.

U.S. Pat. No. 6,410,815 teaches that the performance of the industrial paraxylene separation process largely depend on the adsorbent, its adsorption capacity and the selectively it exhibits for paraxylene in a medium consisting of $C_8$ aromatic compounds, typically paraxylene, metaxylene, orthoxylene, ethylbenzene, and also the aptitude of the desorbents, such as toluene and paradiethylbenzene, to desorb the adsorbed paraxylene therefrom. The selectivity $\alpha_{A/B}$ of the adsorbent for a component A with regard to a component B is defined as the ratio of the concentrations of the compounds in the adsorbed phase divided by the ratio of the concentration of the compounds in the unadsorbed phase at equilibrium:

$$\alpha_{A/B} = A_{ads}/B_{ads} \times B_{liq}/A_{liq}$$

where $A_{ads}$ and $B_{ads}$ are concentrations of compound A and of compound B in the adsorbed phase respectively and $A_{liq}$ and $B_{liq}$ are the concentrations of compound A and of compound B in the fluid phase.

The present invention relates to zeolitic adsorbents, usable in particular for separating paraxylene from a mixture of $C_8$ aromatic compounds, having excellent performance, particularly in terms of selectivity and adsorption capacity for xylenes, said adsorbents being particularly suitable for use in a liquid phase xylene separation method, preferably of the simulated countercurrent type.

The aggregate zeolitic adsorbents as claimed in the present invention comprise:

zeolite X powder exchanged to at least 90% by barium ions alone or by barium ions and potassium ions, the exchangeable sites possibly representing up to ⅓ of the exchangeable sites occupied by the barium plus potassium ions, the possible complement being generally provided by alkali or alkaline-earth ions other than barium and potassium.

zeolite LSX powder exchanged to at least 90% by barium ions alone or by barium ions and potassium ions, the exchangeable sites possibly representing up to ⅓ of the exchangeable sites occupied by the barium plus potassium ions, the possible complement being generally provided by alkali or alkaline-earth ions other than barium and potassium.

and a binder in a proportion lower than or equal to 20% by weight of the total weight of aggregate zeolitic adsorbent.

Unless otherwise indicated, in the following discussion, the expression "between" means "between in the broad sense".

In the context of the present invention, zeolite X means a type X zeolite (faujasite) having a Si/Al atomic ratio strictly higher than 1.15 and lower than or equal to 1.5, preferably between 1.2 and 1.4 and advantageously between 1.2 and 1.3.

According to a preferred embodiment, the zeolite X of the aggregates according to the invention essentially consists of crystals having a mean (number) diameter measured by SEM and counting, lying broadly between 0.1 μm to 4 μm, preferably between 0.1 μm and 3 μm, and advantageously between 0.1 μm and 2 μm.

In the context of the present invention, zeolite LSX (abbreviation of Low Silica X meaning zeolite X with a low silica content), here means a type X zeolite (faujasite) having a Si/Al atomic ratio of between 1 and 1.15, preferably between equal to 1.00±0.05; the values lower than 1 reflect the analytical uncertainties on the measurement of this ratio, and the higher values, either the same analytic uncertainty, or a tolerable difference impurity of the product.

According to a preferred embodiment, the zeolite LSX of the aggregates according to the invention essentially consists of crystals having a mean (number) diameter measured by SEM and counting, of between 0.1 μm and 7 μm, preferably between 0.1 μm and 4 μm, advantageously between 0.1 μm and 3 μm and even more advantageously between 0.1 μm and 2 μm.

In the context of the present invention, binder means an inert inorganic matrix in the context of adsorption, comprising amorphous materials such as silica, mixtures of silica and alumina and/or compounds such as clays. It is not outside the scope of the present invention if this matrix contains zeolitic crystalline materials other than zeolite X and zeolite LSX as defined previously in a quantity not exceeding 5% of the total weight of the aggregate.

For the zeolitic adsorbents according to the invention, the following two efficiency criteria (C.E.) are defined:

$$C.E._{PX/MX} = \alpha_{PX/MX} \times V_{Dub}$$

and $$C.E._{PX/EB} = \alpha_{PX/EB} \times V_{Dub}$$

where $\alpha_{PX/MX}$ and $\alpha_{PX/EB}$ are the selectivities between paraxylene and metaxylene and between paraxylene and ethylbenzene respectively, and where $V_{Dub}$ is the Dubinin volume, which is an estimate of the microporous volume, measured by the method described below, by nitrogen adsorption at 77 K.

The Dubinin volume is calculated from the Dubinin-Radushkevich equation, as described by Lowell et al in "Characterization of Porous Solids and Powders: Surface Area, Pore Size and Density", chapter 9, "Micropore Analysis", pages 143-145:

$$\log V = \log V_0 - D \left( \log \frac{P}{P_0} \right)^2$$

which relates the volume V of nitrogen adsorbed on the adsorbent material at the gauge pressure $P/P_0$. The Dubinin volume is the volume $V_0$, maximum volume of nitrogen vapor that can be condensed in the micropores of the adsorbent material. It is expressed in $cm^3$ of nitrogen vapor (related to standard conditions) per gram of adsorbent.

The Dubinin volume is then calculated from the volume $V_0$ of gas, which is then converted to the volume of liquid; it is expressed in $cm^3$ per gram of adsorbent, and corresponds to the microporous volume available for adsorption.

Prior to the measurement, the sample is pretreated at 500° C. for 12 hours under vacuum ($P<5.10^{-6}$ Torr; or $6.7.10^{-4}$ Pa). The measurement is then taken on a Micromeritics ASAP 2010 M type apparatus. The isotherm is plotted using a pressure table of at least 35 points between 0.01 and 1 $P/P_0$. The value of log V is plotted on a diagram as a function of $(\log(P/P_0))^2$. The Dubinin volume is obtained from the x-axis at the origin of the linear regression line of the points of which $(\log(P/P_0))^2$ is between 1 and 2 (or $0.039<P/P_0<0.1$). The measurement uncertainty is ±0.003.

Measurements taken on adsorbents according to the invention in various proportions of zeolite X and zeolite LSX and with a given fixed binder content show that the two above-mentioned efficiency criteria (C.E.) are significantly higher for mixtures having LSX/X molar ratios of between 0.1 and 10, preferably between 0.25 and 4.0, and even more preferably between 0.5 and 2.0 in comparison with adsorbents only containing zeolite X and binder and to adsorbents only containing zeolite LSX and binder. Each ratios are preferably between 0.5 and 2.0 and even more preferably between 0.54 and 1.86 compared to the adsorbents only containing zeolite X and binder and two adsorbents containing only zeolite LSX and binder.

The invention also relates to a method for preparing aggregates according to the invention which comprises the following steps:

a) agglomeration of a mixture consisting of zeolite LSX powder and zeolite X powder in a LSX/X ratio carrying between 0.1 and 10 and preferably between 0.25 and 4.0, and even more preferably between 0.5 and 2.0 with an agglomeration binder, preferably whereof at least part of the binder contains one or more zeolitizable clays (zeolitizable portion), preferably at least 80% by weight, followed by shaping, drying and calcination, b) an optional step of zeolitization of the zeolitizable portion of the binder by the action of a basic alkaline solution.

c) replacement of at least 90% of all the exchangeable sites of the aggregate by barium, followed by washing and drying of the product thus treated, d) possibly replacement of no more than 33% of all the exchangeable sites of the aggregate by potassium, followed by washing and drying of the product thus treated, and e) optional activation of the product obtained.

Preferably, the preparation method according to the invention essentially consists of steps a) and c) and then e), or a) to e) as previously defined.

The agglomeration and shaping (step a)) can be carried out by any technique known to a person skilled in the art, such as extrusion, compaction, agglomeration.

The agglomeration binder essentially has the role of the shaping and agglomeration of the zeolite powders. Preferably, the binder is inert in the context of adsorption. The agglomeration binder used may contain clays such attapulgite, kaolinite, sepiolite, bentonite, montmorillonite.

In the case of the method in which step a) is followed by the zeolitization step b), the agglomeration binder contains a zeolitizable portion, that is, one or more zeolitizable clays, preferably 80% to 100% of the total weight of binder. Zeolitizable clays generally belong to the family of kaolinite, halloysite, nacrites, dickites, kaolins and/or metakaolins, to which a silica source may be added. Kaolin is commonly used. The calcination that follows drying is carried out at a temperature generally between 500 and 600° C.

Furthermore, in step a), apart from the zeolite powder and agglomeration binder, additives may also be used, for example pore forming agents and/or additives for facilitating the agglomeration and/or for improving the hardening of the aggregates formed.

The zeolite X powder used in step a) may be produced by the synthesis of crystals in zeolite X exchanged with sodium, also called zeolite NaX or 13 X, but it is not outside the scope of the invention to use a powder having undergone one or more cationic exchanges, between the synthesis in NaX form and its use in step a).

The optional source of silica may be colloidal silica, silicate, diatomacious earth, perlite, fly ash, sand and/or any other form of silica.

The zeolite LSX powder used in step a) may be produced by the synthesis of zeolite crystals in NaKLSX form, but it is not outside the scope of the invention to use a powder having undergone one or more cationic exchanges, between the synthesis in NaKLSX form and its use in step a).

The optional zeolitization step b) has the purpose in particular of increasing the adsorption capacity of the aggregate zeolitic adsorbents. It is only effective if the agglomeration binder contains one or more zeolitizable clays.

The zeolitization may be carried out by immersing the product issuing from step a) in a basic alkaline solution, preferably aqueous, for example an aqueous solution of caustic soda or a mixture of caustic soda and caustic potash, of which the concentration is preferably higher than 0.5 M. Said concentration is generally lower than 3 M, preferably lower than 2 M, advantageously lower than 1 M. The zeolitization preferably takes place hot (temperature above ambient temperature) typically at temperatures of about 80-100° C., in order to improve the kinetics of the process and to reduce the immersion times to less than 8 hours, but it is not outside the scope of the invention to operate at lower temperatures.

According to this procedure, the zeolitization of at least 50%, and preferably at least 70 to 82% by weight of the zeolitizable clay(s) contained in the binder is easily obtained. This is followed by a water washing followed by drying.

Step c) of exchange with barium of the cations of the zeolite takes place by contacting the aggregates issuing from optional step b), or from step a), or from optional step d) with a barium salt, such as $BaCl_2$ in aqueous solution at a temperature of between ambient temperature and 100° C., and preferably between 80 and 100° C. To obtain a high barium exchange rate, i.e. higher than 90%, rapidly, it is preferable to operate with a large excess of barium with regard to the cations of the aggregate which are to be exchanged, typically such that the Ba/Al ratio is about 5 to 6, by proceeding with successive exchanges in order to reach the target minimum exchange rate of at least 90% and preferably at least 95%. Throughout the text, the exchange rates are calculated in equivalents and not in molarity.

The optional exchange with potassium (step d)) can be carried out before and/or after the exchange with barium (step c)) or simultaneously, using a solution containing the barium and potassium ions. It is also possible to agglomerate a mixture of powder of zeolite X and of zeolite LSX already containing potassium ions and eliminate step d) (or not).

The activation (step e)), the final step of the method for obtaining the adsorbents according to the invention, is intended to fix the moisture content and the ignition loss of the adsorbent within optimal limits. This is generally done by thermal activation which is preferably carried out between 200° C. and 300° C. for a certain length of time, typically from 1 to 6 hours, according to the desired moisture content and ignition loss, and depending on the intended use of the adsorbent.

The invention also relates to the uses of at least one of the zeolitic adsorbents described above as adsorption agents suitable for advantageously replacing the adsorption agents described in the literature based on zeolite X or based on zeolite LSX, exchanged with barium or exchanged with barium and potassium, and particularly to the uses listed below:
  separation of $C_8$ aromatic isomers and particularly xylenes,
  separation of sugars,
  separation of polyhydric alcohols,
  separation of isomers of substituted toluene such as nitrotoluene, diethyltoluene, toluenediamine,
  separation of cresols,
  separation of dichlorobenzenes.

The invention relates in particular to an improvement of the method for recovering paraxylene from aromatic $C_8$ isomer cuts by using, as a paraxylene adsorption agent, and a zeolitic adsorbent according to the invention, used in liquid phase methods and also in gas phase methods.

The invention relates in particular to a method for producing high purity paraxylene from an aromatic hydrocarbon feedstock containing isomers with 8 carbon atoms comprising the following steps:
  a) a step of contacting the feedstock with the bed of adsorbent according to the invention, under appropriate adsorption conditions, in order to preferably adsorb the paraxylene,
  b) a step of contacting the adsorbent bed with a desorbent, which is preferably either toluene or paradiethylbenzene, under appropriate desorption conditions,
  c) a step of withdrawing from the adsorbent bed a stream containing the desorbent and the least selectively adsorbed products of the feedstock,
  d) a step of withdrawal from the adsorbent bed of a stream containing the desorbent and the paraxylene,
  e) a separation of the stream issuing from step c) into a first stream containing the desorbent and a second stream containing the least selectively adsorbed products of the feedstock,
  f) a separation of the stream issuing from step d) into a first stream containing the desorbent and the second stream containing the paraxylene in a purity higher than or equal to 75% and preferably higher than or equal to 99.7%.

The method may also optionally include the following step:
  g) a step of crystallization in a crystallizer consisting of the crystallization of the paraxylene issuing from step f), in order to obtain on the one hand crystals of paraxylene impregnated with their mother liquor, and on the other a mother liquor which may partly, or completely, be recycled in a mixture with the fresh feedstock at the inlet of the simulated moving bed adsorption unit, h) a step of washing the crystals issuing from step g) after which the paraxylene is recovered in a purity of at least 99.7%, and preferably at least 99.8%.

The desired product can thus be separated by preparative adsorption liquid chromatography (in batches) advantageously in a simulated moving bed, that is, in simulated countercurrent or simulated cocurrent, and more particularly in simulated countercurrent.

The chromatographic separation in simulated moving bed in simulated countercurrent is well known in the prior art. In general, a simulated moving bed separation unit comprises at least one adsorption column containing a plurality of beds of an adsorbent, interconnected in a closed loop. The simulated moving bed separation unit comprises at least three chromatographic zones, and optionally four or five, each of these zones consisting of at least one bed or a portion of column and lying between two successive feed or withdrawal points.

Typically, at least one feedstock to be fractionated and one desorbent (sometimes called eluant) are fed and at least raffinate and one extract are withdrawn. The feed and withdrawal points are modified over time, typically shifted towards the bottom of a bed and synchronously.

By definition, each of the operating zones is designated by a number:

Zone 1=zone of desorption of the desired product (contained in the extract) lying between the desorbent injection and the extract withdrawal;

Zone 2=zone of desorption of the compounds of the raffinate, lying between the extract withdrawal and the injection of the feedstock to be fractionated;

Zone 3=zone of adsorption of the desired product, lying between the feedstock injection and the raffinate withdrawal, and Zone 4 located between the raffinate withdrawal and the desorbent injection.

The operating conditions of an industrial adsorption unit of the simulated countercurrent type are generally as follows:

number of beds 6 to 30;
number of zones at least 4;
temperature 100 to 250° C., preferably 150 to 190° C.;
pressure between the bubble point pressure of xylenes at the temperature of the process and 3 MPa;
ratio of desorbent to feedstock flow rate 0.7 to 2.5 (for example 0.9 to 1.8 for a stand alone adsorption unit and 0.7 to 1.4 for an adsorption unit combined with a crystallization unit);
recycle rate from 2.5 to 12, preferably 3.5 to 6.

Reference can be made to the teaching of U.S. Pat. No. 2,985,589, U.S. Pat. No. 5,284,992 and U.S. Pat. No. 5,629,467.

The operating conditions of an industrial simulated cocurrent adsorption unit are generally the same as those operating in simulated countercurrent, with the exception of the recycle rate which is generally between 0.8 and 7. Reference can be made to U.S. Pat. No. 4,402,832 and U.S. Pat. No. 4,498,991.

The desorption solvent may be a desorbent having a boiling point lower than that of the feedstock, such as toluene, but also a desorbent of which the boiling point is higher than that of the feedstock, such as paradiethylbenzene (PDEB). The selectivity of the adsorbents according to the invention for adsorbing the paraxylene contained in the $C_8$ aromatic cuts is optimal when their ignition loss measured at 900° C. is generally between 4.0 and 8.0%, and preferably between 4.7 and 6.7%. Water and a little carbon dioxide are included in the ignition loss.

One of the techniques of choice for characterizing the adsorption of molecules in the liquid phase on a porous solid is to obtain a breakthrough. In his work "Principles of Adsorption and Adsorption Processes", Ruthven defines the technique of breakthrough curves as the analysis of the injection of an echelon of adsorbable constituents.

The present invention is now described by means of the following examples, which are intended to illustrate certain embodiments of the invention, but without limiting the scope thereof as claimed in the appended claims.

EXAMPLE 1

Comparative 840 g (expressed as calcined equivalent) of a zeolite X powder having a Si/Al ratio=1.25, and having a mean crystal size of 1.6 µm, is aggregated by intimately mixing it with 160 g of kaolin (expressed as calcined equivalent) with an adequate quantity of water to ensure the formation of aggregates by extrusion. The extrudates are dried, crushed in order to recover the aggregates having an equivalent diameter of 0.7 mm, and then activated at 550° C. for 2 hours under nitrogen stream.

These granules are exchanged by means of a 0.5 M barium chloride solution at 95° C. in 4 steps. At each step, the ratio of solution volume to solid mass is 20 mL/g and the exchange is continued for 4 hours each time. Between each exchange, the solid is washed several times in order to remove the excess salt. It is then activated at a temperature of 200° C. for two hours under nitrogen stream.

The barium exchange rate is 97% and the ignition loss (measured at 900° C.) is 6.5%.

The microporous volume measured by the Dubinin method by nitrogen adsorption at 77K after pretreatment at 500° C. for 12 hours under vacuum is 0.235 cm$^3$/g.

EXAMPLE 2

Comparative 900 g (expressed as calcined equivalent) of a zeolite X powder having a Si/Al ratio=1.25, and having a mean crystal size of 1.6 µm, is aggregated by intimately mixing it with 170 g of kaolin (expressed as calcined equivalent), 70 g of colloidal silica sold under the trade name Klebosol® 30 (containing 30% by weight of $SiO_2$ and 0.5% of $Na_2O$) and the quantity of water to ensure the formation of aggregates by extrusion. The extrudates are dried, crushed in order to recover the aggregates having an equivalent diameter of 0.7 mm, and then activated at 550° C. for 2 hours under nitrogen stream.

200 g of granules thus obtained are placed in a glass reactor provided with a double jacket regulated at a temperature of 100±1° C. and 1.5 L of an aqueous solution of caustic soda having a concentration of 100 g/L is added, and the reaction medium is left with stirring for 3 hours. The granules are then washed in 3 successive operations followed by drainage of the reactor. The effectiveness of the washing is verified by measuring the final pH of the wash water, which must be between 10 and 10.5.

Barium exchange is then carried out under the identical operating conditions as those in example 1 followed by washing and then drying at 80° C. for two hours, and finally activation at 200° C. for 2 hours under nitrogen stream.

The barium exchange rate is 95% and the ignition loss (measured at 900° C.) is 6.5%.

The microporous volume measured by the Dubinin method by nitrogen adsorption at 77K after pretreatment at 500° C. for 12 hours under vacuum is 0.256 cm³/g.

EXAMPLE 3

Comparative 840 g (expressed as calcined equivalent) of a zeolite X powder having a Si/Al ratio=1.02, and having a mean crystal size of 2.6 μm, is aggregated by intimately mixing it with 160 g of kaolin (expressed as calcined equivalent) with an adequate quantity of water to ensure the formation of aggregates by extrusion. The extrudates are dried, crushed in order to recover the aggregates having an equivalent diameter of 0.7 mm, and then calcined at 550° C. for 2 hours under nitrogen stream.

The barium exchange is carried out under identical operating condition to those in example 1, with the exception of the concentration of the BaCl₂ solution, which is 0.7 M followed by washing and then drying at 80° C. for two hours, and finally activation at 200° C. for 2 hours under nitrogen stream.

The barium exchange rate is 98% and the ignition loss (measured at 900° C.) is 6.5%. The microporous volume measured by the Dubinin method by nitrogen adsorption at 77K after pretreatment at 500° C. for 12 hours under vacuum is 0.205 cm³/g.

EXAMPLE 4

Comparative 840 g (expressed as calcined equivalent) of a zeolite X powder having a Si/Al ratio=1.01, and having a mean crystal size of 2.6 μm, and 160 g of kaolin (expressed as calcined equivalent), are intimately mixed and agglomerated with an adequate quantity of water to ensure the formation of aggregates by extrusion. The extrudates are dried, crushed in order to recover the aggregates having an equivalent diameter of 0.7 mm, and then activated at 550° C. for 2 hours under nitrogen stream.

200 g of granules thus obtained are placed in a glass reactor provided with a double jacket regulated at a temperature of 95±1° C. and 700 mL of an aqueous solution of caustic soda having a concentration of 220 g/L is added, and the reaction medium is left with stirring for 3 hours.

The granules are then washed in 4 successive operations followed by drainage of the reactor. The effectiveness of the washing is verified by measuring the final pH of the wash water, which must be between 10 and 10.5.

Barium exchange is then carried out under the identical operating conditions as those in example 1 followed by washing and then drying at 80° C. for 2 hours, and finally activation at 200° C. for 2 hours under nitrogen stream.

The barium exchange rate is 97% and the ignition loss is 6.5%. The microporous volume measured by the Dubinin method by nitrogen adsorption at 77K after pretreatment at 500° C. for 12 hours under vacuum is 0.235 cm³/g.

EXAMPLE 5

According to the Invention

Three mixtures are prepared of powder consisting of zeolite X powder, having a Si/Al ratio=1.25, and a mean crystal size of 1.6 μm, and zeolite LSX powder, having a Si/Al ratio=1.01 and a mean crystal size of 2.6 μm, in LSX/X molar ratios as follows: 0.54; 1 and 1.86.

900 g (expressed as calcined equivalent) of each of these mixtures are then agglomerated by mixing them intimately with 170 g of kaolin (expressed as calcined equivalent) and an adequate quantity of water to ensure the formation of aggregates by extrusion. The extrudates are dried, crushed in order to recover the aggregates having an equivalent diameter of 0.7 mm, and then activated at 550° C. for 2 hours under nitrogen stream.

The barium exchange is carried out under identical operating conditions to those of example 1. The barium exchange rate of these 3 products is given in Table 1 below. The microporous volumes measured by the Dubinin method by nitrogen adsorption at 77 K after pretreatment at 500° C. for 12 hours under vacuum, are 0.229 cm³/g for the sample with the LSX/X ratio=0.54, 0.236 for the sample having the LSX/X ratio=1 and 0.230 for the sample having the LSX/X ratio=1.86.

TABLE 1

|  | LSX/X = 0.54 | LSX/X = 1 | LSX/X = 1.86 |
|---|---|---|---|
| Barium exchange rate (%) | 96 | 97 | 97 |

EXAMPLE 6

The 3 samples prepared in example 5 are activated identically in a single step at 200° C. for 2 hours under nitrogen stream in order to fix an ignition loss (measured at 900° C.) of 6.5%.

These 3 samples and the samples prepared in examples 1 and 3 having the same ignition loss are then evaluated by a frontal chromatography device (breakthrough technique) to determine the paraxylene-metaxylene selectivity or the paraxylene-ethylbenzene selectivity respectively.

The breakthrough technique consists in injecting a feedstock containing equal quantities of paraxylene and metaxylene or of paraxylene and ethylbenzene and a small quantity of unadsorbable tracer, in echelon form, into a column filled with zeolite sieve resaturated with solvent and at the temperature of the method. The response to this injection is then monitored over time.

For this purpose, the effluent leaving the column is sampled in small volume vials using a fraction collector. The content of the vials is then analyzed by gas chromatography. The result obtained is expressed in graphic form: composition of the various constituents contained in the effluent as a function of time (or of eluted volume). This curve can be used to characterize the thermodynamic and kinetic behavior of the sieve. It serves to determine, inter alia, the separation selectivity between the constituents A and B $\alpha_{A/B}$ as previously defined.

The microporous volume is also measured by the Dubinin method by nitrogen adsorption at 77 K after pretreatment at 500° C. for 12 hours under vacuum. The Dubinin volumes thus obtained as given in Table 2, together with the results for selectivity and efficiency.

It is found that, surprisingly, the efficiency criteria of the samples comprising mixtures of X crystals and LSX crystals are substantially higher than those of the samples comprising only one of the two structures.

TABLE 2

| Sieve | $\alpha_{PX/MX}$[1] | $\alpha_{PX/EB}$[2] | $V_{D_{ub}}$[3] (cm³/g) | C.E.$_{PX/MX}$[4] | C.E.$_{PX/EB}$[5] |
|---|---|---|---|---|---|
| Example 1 | 3.3 | 2.2 | 0.235 | 0.776 | 0.517 |
| Example 5 LSX/X = 0.54 | 3.65 | 2.55 | 0.229 | 0.836 | 0.584 |
| Example 5 LSX/X = 1 | 3.7 | 2.9 | 0.236 | 0.873 | 0.684 |
| Example 5 LSX/X = 1.86 | 3.75 | 2.9 | 0.230 | 0.863 | 0.667 |
| Example 3 | 4.03 | 2.9 | 0.205 | 0.826 | 0.595 |

[1]selectivity between paraxylene and metaxylene
[2]selectivity between paraxylene and ethylbenzene
[3]Dubinin volume
[4]PX/MX efficiency criterion
[5]PX/EB efficiency criterion

EXAMPLE 7

According to the Invention

A mixture is prepared having a LSX/X molar ratio=1 of zeolite X powder, having a Si/Al ratio=1.25, and a mean crystal size of 1.6 μm, and zeolite LSX powder, having a Si/Al ratio=1.01 and a mean crystal size of 2.6 μm.

900 g (expressed as calcined equivalent) of each of these mixtures are then agglomerated by mixing them intimately with 170 g of kaolin (expressed as calcined equivalent), 70 g of colloidal silica sold under the trade name Klebosol® 30 (containing 30% by weight of SiO$_2$ and 0.5% of Na$_2$O) and the quantity of water to ensure the formation of aggregates by extrusion. The extrudates are dried, crushed in order to recover the aggregates having an equivalent diameter of 0.7 mm, and then activated at 550° C. for 2 hours under nitrogen stream.

200 g of granules thus obtained are placed in a glass reactor provided with a double jacket regulated at a temperature of 100±1° C. and 1.5 L of an aqueous solution of caustic soda having a concentration of 100 g/L is added, and the reaction medium is left with stirring for 3 hours. The granules are then washed in successive operations followed by drainage of the reactor. The effectiveness of the washing is verified by measuring the final pH of the wash water, which must be between 10 and 10.5.

Barium exchange is then carried out under the identical operating conditions as those in example 1 followed by washing and then drying at 80° C. for two hours, and finally activation at 200° C. for 2 hours under nitrogen stream in order to fix the ignition loss at 6.5% as in example 5.

The barium exchange rate is 97.2%.

These samples were tested on the frontal chromatography device also described in example 6, together with two comparative 100% X and 100% LSX samples prepared respectively according to examples 2 and 4.

The microporous volume is also measured by the Dubinin method by nitrogen adsorption at 77 K after pretreatment at 500° C. for 12 hours under vacuum. The Dubinin volumes thus obtained as given in Table 3.

The results for selectivity and efficiency criteria are given in Table 3, which also resumes the results of Table 2 concerning the adsorbents described in example 6.

TABLE 3

| Sieve | $\alpha_{PX/MX}$[1] | $\alpha_{PX/EB}$[2] | $V_{D_{ub}}$[3] (cm³/g) | C.E.$_{PX/MX}$[4] | C.E.$_{PX/EB}$[5] |
|---|---|---|---|---|---|
| Example 1 | 3.3 | 2.2 | 0.235 | 0.776 | 0.517 |
| Example 2 | 3.33 | 2.25 | 0.256 | 0.852 | 0.576 |
| Example 5 LSX/X = 1 | 3.70 | 2.9 | 0.236 | 0.873 | 0.684 |
| Example 7 | 3.65 | 2.92 | 0.255 | 0.931 | 0.745 |
| Example 3 | 4.03 | 2.9 | 0.205 | 0.826 | 0.595 |
| Example 4 | 3.98 | 2.92 | 0.235 | 0.935 | 0.686 |

[1]selectivity between paraxylene and metaxylene
[2]selectivity between paraxylene and ethylbenzene
[3]Dubinin volume
[4]PX/MX efficiency criterion
[5]PX/EB efficiency criterion The results from Tables 2 and 3 show that, surprisingly, the efficiency criteria are much higher with the aggregates according to the invention based on an X/LSX mixture, in comparison to sieves exclusively composed of X or of LSX.

FIG. 1 presents the variation in the Dubinin volume (on the y-axis) as a function of the level of zeolite LSX present in the aggregate according to the invention based on an X/LSX mixture (on the x-axis).

The value 0 on the x-axis corresponds to an aggregate based on zeolite X alone, whereas the value 1 corresponds to an aggregate based on zeolite LSX alone.

The graph from FIG. 1 shows the unexpected effect on the Dubinin volume, when aggregates based on an X/LSX mixture according to the invention are obtained: the Dubinin volumes obtained are greater than those logically expected, which are represented by the straight dotted line.

EXAMPLE 8

In order to evaluate the performance of the sieves as a function of ignition loss, various activations were carried out of the sample only containing X crystals (prepared according to example 2) and the sample having the LSX/X molar ratio=1, prepared by the method described in example 3:

activation at a temperature of 230° C. for 2 hours under nitrogen steam in order to fix an ignition loss (measured at 900° C.) of 5%;

activation at a temperature of 170° C. for 2 hours under nitrogen stream in order to fix an ignition loss (measured at 900° C.) of 8%.

A sample comprising only LSX crystals (prepared according to example 4) was activated at a temperature of 200° C. for 2 hours under nitrogen stream in order to fix an ignition loss (measured at 900° C.) of 6.5%.

Samples were tested on the frontal chromatography device also described in example 6.

Table 4 below summarizes the PX/MX selectivities and the xylene adsorption capacities (cm³/g) obtained for the sieve exclusively comprising X and that having the LSX/X molar ratio=1.

TABLE 4

| | Capacity[1] | $\alpha_{PX/MX}$[2] | $\alpha_{PX/EB}$[3] |
|---|---|---|---|
| | Ignition Loss = 5% | | |
| 100% X | 0.225 | 3.5 | 2.5 |
| LSX/X = 1 | 0.229 | 3.7 | 3.12 |
| | Ignition Loss = 6.5% | | |
| 100% X | 0.190 | 3.33 | 2.25 |
| LSX/X = 1 | 0.205 | 3.65 | 2.92 |
| 100% LSX | 0.178 | 3.98 | 2.92 |

TABLE 4-continued

|  | Capacity[1] | $\alpha_{PX/MX}$[2] | $\alpha_{PX/EB}$[3] |
|---|---|---|---|
|  | Ignition Loss = 8% | | |
| 100% X | 0.172 | 3.3 | 2.1 |
| LSX/X = 1 | 0.197 | 3.6 | 2.7 |

[1]quantity of xylene adsorbed in cm³/g
[2]selectivity between paraxylene and metaxylene
[3]selectivity between paraxylene and ethylbenzene For all the ignition losses tested, the performance of the aggregates based on the X/LSX mixture is better than the performance of the sieves only containing zeolite X and that of the sieves only containing zeolite LSX under equivalent conditions.

EXAMPLE 9

A mixture is prepared having a LSX/X molar ratio=1 of zeolite X powder, having a Si/Al ratio=1.25, and a mean crystal size of 1.6 μm, and zeolite LSX powder, having a Si/Al ratio=1.01 and a mean crystal size of 1.6 μm.

900 g (expressed as calcine equivalent) of each of these mixtures are then agglomerated by mixing them intimately with 170 g of kaolin (expressed as calcined equivalent) and the adequate quantity of water to ensure the formation of aggregates by extrusion. The extrudates are dried, crushed in order to recover the aggregates having an equivalent diameter of 0.7 mm, and then activated at 550° C. for 2 hours under nitrogen stream.

200 g of granules thus obtained are placed in a glass reactor provided with a double jacket regulated at a temperature of 100±1° C. and 1.5 L of an aqueous solution of caustic soda having a concentration of 100 g/L is added, and the reaction medium is left with stirring for 3 hours. The granules are then washed in 3 successive operations followed by drainage of the reactor. The effectiveness of the washing is verified by measuring the final pH of the wash water, which must be between 10 and 10.5.

Barium exchange is then carried out under the identical operating conditions as those in example 1 followed by washing and then drying at 80° C. for two hours, and finally activation at 200° C. for 2 hours under nitrogen stream in order to fix the ignition loss at 6.5% as in example 5.

The barium exchange rate is 97%.

EXAMPLE 10

Comparative

A mixture is prepared consisting of 50% of granules prepared according to example 2 of the present invention and 50% of LSX granules prepared according to example 4.

Barium exchange is then carried out under the identical operating conditions as those in example 1 followed by washing and then drying at 80° C. for two hours, and finally activation at 200° C. for 2 hours under nitrogen stream in order to fix the ignition loss at 6.5% as in example 5.

The barium exchange rate is 97.2%.

This mixture of X granules and LSX granules is then evaluated by a frontal chromatography device (breakthrough technique) to determine the paraxylene-metaxylene selectivity or the paraxylene-ethylbenzene selectivity respectively.

The results of this tests are given in Table 5.

TABLE 5

| Sieve | $\alpha_{PX/MX}$[1] | $\alpha_{PX/EB}$[2] | $V_{Dub}$[3] (cm³/g) | C.E.$_{PX/MX}$[4] | C.E.$_{PX/EB}$[5] |
|---|---|---|---|---|---|
| Mixture of X granules and LSX granules | 3.3 | 2.2 | 0.240 | 0.790 | 0.527 |

[1]selectivity between paraxylene and metaxylene
[2]selectivity between paraxylene and ethylbenzene
[3]Dubinin volume
[4]PX/MX efficiency criterion
[5]PX/EB efficiency criterion The results in Table 5 show that the simple mixture of X aggregates and LSX aggregates does not suffice to obtain the synergy observed for the mixture of X and LSX crystals in one and the same aggregate.

The invention claimed is:

1. An aggregate zeolitic adsorbent comprising:
   zeolite X powder exchanged to at least 90% by barium ions alone or by barium ions and potassium ions, the exchangeable sites representing up to ⅓ of the exchangeable sites occupied by the barium plus potassium ions, remaining sites being occupied by alkali or alkaline-earth ions other than barium and potassium,
   zeolite LSX powder exchanged to at least 90% by barium ions alone or by barium ions and potassium ions, the exchangeable sites representing up to ⅓ of the exchangeable sites occupied by the barium plus potassium ions, remaining sites being occupied by alkali or alkaline-earth ions other than barium and potassium, wherein the molar ratio of the zeolite LSX concentration to the zeolite X concentration is between 0.1 and 10;
   and a binder in a proportion lower than or equal to 20% by weight of the total weight of the aggregate zeolitic adsorbent.

2. The adsorbent as claimed in claim 1, wherein the molar ratio of the zeolite LSX concentration to the zeolite X concentration is between 0.5 and 2.0.

3. The adsorbent as claimed in claim 1, wherein the zeolite X essentially consists of crystals having a mean (number) diameter measured by SEM and counting, of between 0.1 and 4 μm.

4. The adsorbent as claimed in claim 1, wherein the zeolite LSX essentially consists of crystals having a mean (number) diameter measured by SEM and counting, of between 0.1 μm and 7 μm.

5. A method for preparing an adsorbent as claimed in claim 1, comprising the following steps:
   a) agglomeration of a mixture consisting of zeolite LSX powder and zeolite X powder in a LSX/X ratio carrying between 0.1 and 10 with an agglomeration binder, followed by shaping, drying and calcination, and
   b) replacement of at least 90% of all the exchangeable sites of the aggregate by barium, followed by washing and drying of the product thus treated.

6. A method for separating C$_8$ aromatic isomers, sugars, polyhydric alcohols, isomers of substituted toluenes, cresols, or dichlorobenzenes, the method comprising a step of contacting a feed stock with the adsorbent as claimed in claim 1.

7. A method as claimed in claim 6, wherein a paraxylene is recovered from aromatic C$_8$ isomer cuts.

8. The method as claimed in claim 7, which is carried out in liquid phase.

9. The method as claimed in claim 7, which is carried out in gas phase.

10. The method for recovering paraxylene as claimed in claim 7, which is of the simulated moving bed type.

11. The method for recovering paraxylene as claimed in claim 7, which is of the simulated countercurrent type.

12. The method for recovering paraxylene as claimed in claim 7, which is of the simulated cocurrent type.

13. The method for recovering paraxylene as claimed in claim 7, further comprising contacting the absorbent with a desorbent, wherein the desorbent is toluene or paradiethylbenzene.

14. The method for recovering paraxylene, as claimed in claim 7, wherein the zeolitic adsorbent has an ignition loss measured at 900° C. of between 4.0 and 8%.

15. The adsorbent as claimed in claim 1, wherein the molar ratio of the zeolite LSX concentration to the zeolite X concentration is between 0.25 and 4.

16. The adsorbent as claimed in claim 1, wherein the molar ratio of the zeolite LSX concentration to the zeolite X concentration is between 0.54 and 1.86.

17. The adsorbent as claimed in claim 1, wherein the zeolite X essentially consists of crystals having a mean (number) diameter measured by SEM and counting, of between 1 and 3 μm.

18. The adsorbent as claimed in claim 1, wherein the zeolite X essentially consists of crystals having a mean (number) diameter measured by SEM and counting, of between 0.1 and 2 μm.

19. The adsorbent as claimed in claim 1, wherein the zeolite LSX essentially consists of crystals having a mean (number) diameter measured by SEM and counting, of between 0.1 μm and 4 μm.

20. The adsorbent as claimed in claim 1, wherein the zeolite LSX essentially consists of crystals having a mean (number) diameter measured by SEM and counting, of between 0.1 μm and 3 μm.

21. The adsorbent as claimed in claim 1, wherein the zeolite LSX essentially consists of crystals having a mean (number) diameter measured by SEM and counting, of between 0.1 μm and 2 μm.

22. The method of claim 5, wherein the LSX/X ratio is between 0.25 and 4.0.

23. The method of claim 5 wherein the LSX/X ration is between 0.5 and 2.0.

24. The method of claim 5, wherein at least part of the binder contains one or more zeolitizable clays.

25. The method of claim 24, wherein the binder contains at least 80% by weight of the one or more zeolitizable clays.

26. The method of claim 22, further comprising zeolitization of the zeolitizable portion of the binder by the action of a basic alkaline solution, after step a).

27. The method of claim 5, further comprising replacement of no more than 33% of all the exchangeable sites of the aggregate by potassium, followed by washing and drying of the product thus treated, after step b).

28. The method of claim 27, further comprising an activation step after the washing and drying of the product.

29. The method of claim 5, further comprising an activation step, after step b).

30. The method of claim 14, wherein the zeolitic adsorbent has an ignition loss measured at 900° C. of between 4.7 and 6.7%.

31. The method of claim 6, wherein the $C_8$ aromatic isomers are xylenes.

\* \* \* \* \*